(12) United States Patent
White

(10) Patent No.: US 8,124,805 B2
(45) Date of Patent: Feb. 28, 2012

(54) ALLYL ACETATE HYDROFORMYLATION PROCESS

(75) Inventor: Daniel F. White, West Chester, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 12/592,457

(22) Filed: Nov. 25, 2009

(65) Prior Publication Data

US 2011/0124904 A1    May 26, 2011

(51) Int. Cl.
*C07C 67/02*    (2006.01)
(52) U.S. Cl. ........................................ 560/266
(58) Field of Classification Search .................. None
See application file for complete search history.

(56) References Cited

U.S. PATENT DOCUMENTS

| 4,005,113 A * | 1/1977 | Smith | 549/508 |
| 6,225,509 B1 * | 5/2001 | Dubner et al. | 568/454 |

FOREIGN PATENT DOCUMENTS

| GB | 1 461 831 | 3/1974 |
| GB | 1 493 154 | 8/1975 |
| WO | WO 2005/049537 A1 * | 6/2005 |

* cited by examiner

*Primary Examiner* — Paul A Zucker

(57) ABSTRACT

A process for the production of 4-acetoxybutyraldehyde is described. The process comprises reacting allyl acetate with a mixture of carbon monoxide and hydrogen in the presence of a solvent and a catalyst comprising a rhodium complex and a diphosphine. The diphoshine is a substituted or unsubstituted 2,2'-bis(dihydrocarbylphosphino)diphenyl ether. The process gives a high ratio of 4-acetoxybutyraldehyde:3-acetoxy-2-methylpropionaldehyde.

12 Claims, No Drawings

ALLYL ACETATE HYDROFORMYLATION PROCESS

FIELD OF THE INVENTION

This invention relates to a process for hydroformylating allyl acetate to produce 4-acetoxybutyraldehyde.

BACKGROUND OF THE INVENTION

The hydroformylation of allyl acetate is taught in the prior art. British Pat. Nos. 1,461,831 and 1,493,154, for example, teach processes for preparing butanediols. In the hydroformylation reaction, allyl acetate is reacted with a $CO/H_2$ gas mixture in the presence of a catalyst to form 4-acetoxybutyraldehyde (ABA). The ABA may then be separated from the catalyst, e.g., by water extraction, and hydrolyzed and/or hydrogenated to form 1,4-butanediol (BDO). British Pat. No. 1,461,831 teaches the use of a cobalt or rhodium catalyst in the hydroformylation reaction. British Pat. No. 1,493,154 discloses the use of a catalyst comprising a rhodium complex containing a polymeric phosphorus compound.

One disadvantage of the hydroformylation of allyl acetate is that other co-products or byproducts are also formed in addition to the desired ABA linear product. The hydroformylation of allyl acetate typically produces some 3-acetoxy-2-methylpropionaldehyde (AMPA) branched co-product and $C_3$ byproducts such as acetates of propylene or propane, and $C_4$ byproducts such as butyraldehyde. Although AMPA may be hydrolyzed and/or hydrogenated to produce 2-methyl-1,3-propanediol (MPD), which is a useful material, the MPD co-product reduces the yield of BDO. Formation of $C_3$ byproducts effectively represents another yield loss in the process which can have a severe adverse effect on the process economics.

In sum, new processes for hydroformylating allyl acetate to produce 4-acetoxybutyraldehyde are needed. Particularly valuable processes would result in high ratios of 4-acetoxybutyraldehyde to 3-acetoxy-2-methylpropionaldehyde.

SUMMARY OF THE INVENTION

The invention is a process that comprises reacting allyl acetate with carbon monoxide and hydrogen in the presence of a solvent and a catalyst to produce 4-acetoxybutyraldehyde. The catalyst comprises a rhodium complex and a substituted or unsubstituted 2,2'-bis(dihydrocarbylphosphino)diphenyl ether. The invention surprisingly results in extremely high ratios of 4-acetoxybutyraldehyde product to 3-acetoxy-2-methylpropionaldehyde.

DETAILED DESCRIPTION OF THE INVENTION

The process of the invention comprises hydroformylating allyl acetate in the presence of a solvent and a catalyst. The catalyst comprises a rhodium complex and a substituted or unsubstituted 2,2'-bis(dihydrocarbylphosphino)diphenyl ether (also called the "diphosphine ligand"). 2,2'-Bis(dihydrocarbylphosphino)diphenyl ethers have the general formula:

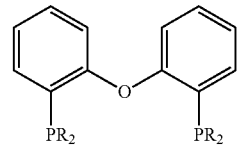

wherein R is an alkyl or aryl group and any of the ring carbons may be substituted or unsubstituted. The R groups may be the same or are different, but preferably are the same. Preferably, R is a $C_6$-$C_{12}$ aryl group or a $C_1$-$C_6$ n-alkyl group, including, e.g., phenyl, tolyl, methyl, ethyl, or n-propyl. More preferably, R is a $C_6$-$C_{12}$ aryl group, such as phenyl or p-tolyl.

Preferred 2,2'-bis(dihydrocarbylphosphino)diphenyl ethers include a substituted or unsubstituted 4,5-bis(dihydrocarbylphosphino)xanthene. 4,5-Bis(dihydrocarbylphosphino)xanthenes have the general formula:

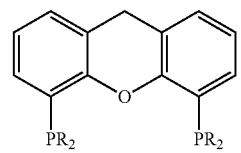

wherein R is an alkyl or aryl group and any of the ring carbons may be substituted or unsubstituted. The R groups may be the same or are different, but preferably are the same. Preferably, R is a $C_6$-$C_{12}$ aryl group or a $C_1$-$C_6$ n-alkyl group, including, e.g., phenyl, tolyl, methyl, ethyl, or n-propyl. More preferably, R is a $C_6$-$C_{12}$ aryl group, such as phenyl or p-tolyl.

The 4,5-bis(dihydrocarbylphosphino)xanthene ligand is more preferably a 9,9-dimethyl-4,5-bis(dihydrocarbylphosphino)xanthene, most preferably 9,9-dimethyl-4,5-bis(diphenylphosphino)xanthene, 9,9-dimethyl-4,5-bis(dimethylphosphino)xanthene, or 9,9-dimethyl-4,5-bis(diethylphosphino)xanthene. In another preferred embodiment, the 4,5-bis(dihydrocarbylphosphino)xanthene ligand is a 2,7-dialkyl-9,9-dimethyl-4,5-bis(diarylphosphino)xanthene, most preferably 2,7-di-tert-butyl-9,9-dimethyl-4,5-bis(diphenylphosphino)xanthene, 2,7-di-tert-butyl-9,9-dimethyl-4,5-bis(dimethylphosphino)xanthene, or 2,7-di-tert-butyl-9,9-dimethyl-4,5-bis(diethylphosphino) xanthene.

The 2,2'-bis(dihydrocarbylphosphino)diphenyl ether may be prepared by any possible method. For instance, it may be prepared by the reaction of a 2,2'-dilithium-diphenyl ether with a chloro(dihydrocarbyl)phosphine.

The catalyst useful in the process of the invention also comprises a rhodium complex. Suitable rhodium complexes contain rhodium attached to ligand groups. The rhodium complex is preferably soluble in the solvent. There are no particular restrictions regarding the choice of ligands attached to the rhodium complex. For example, suitable ligands include hydride, carbonyl, substituted and unsubstituted cyclopentadienyls, 2,4-alkanedionates, trialkyl phosphines, triaryl phosphines, and mixtures thereof. The rhodium complex may also contain diphosphine compounds, including a 2,2'-bis(dihydrocarbylphosphino)diphenyl ether or other known diphosphines. Particularly preferred ligands include carbonyl, acetylacetonate (2,4-pentanedionate), triphenylphosphine, and mixtures thereof. Examples of preferred rhodium complexes include (acetylacetonato) dicarbonylrhodium and tris(triphenylphosphine)rhodium carbonyl hydride.

The rhodium complex can be pre-associated with the 2,2'-bis(dihydrocarbylphosphino)diphenyl ether ligand prior to use in the hydroformylation reaction such that the 2,2'-bis(dihydrocarbylphosphino)diphenyl ether forms part of the rhodium complex, or it can be added separately. However, it is preferable to add the rhodium complex separate from the 2,2'-bis(dihydrocarbylphosphino) diphenyl ether. The molar ratio of the diphosphine ligand:rhodium complex is preferably in the range of 0.5:1 to 5:1.

Although not necessary, the catalyst may additionally comprise a monophosphine compound. The monophosphine compound is in addition to any phosphine ligand that may be associated with the rhodium complex. The monophosphine compound is a trisubstituted phosphine that is represented by the formula:

$(R^1)_3P$ wherein $R^1$ is an aryl or alkyl group. Suitable aliphatic $R^1$ groups include methyl, ethyl, n-butyl, sec-butyl, octyl, and decyl. Suitable aromatic $R^1$ groups include phenyl, tolyl, and naphthyl. The $R^1$ groups may be the same or are different, but preferably are the same. Preferably, the monophosphine is a trisubstituted aryl phosphine. More preferably, the monophosphine is triphenylphosphine or tritolylphosphine. Triphenyl phosphine is particularly preferred.

A reaction solvent is also required for the process of the invention. Typical solvents are those that are capable of solubilizing the rhodium complex. Suitable solvents include any organic solvent having very low or minimal solubility in water. Preferred solvents include $C_5$-$C_{20}$ aliphatic hydrocarbons, $C_6$-$C_{20}$ aromatic hydrocarbons, alcohols, ethers, and mixtures thereof. Particularly preferred solvents include toluene, cyclohexane, methyl t-butyl ether, and mixtures thereof.

Typical reaction conditions for the hydroformylation step are mild to favor the formation of the linear 4-acetoxybutyraldehyde (ABA) rather than branched 3-acetoxy-2-methylpropionaldehyde (AMPA) co-product. Reaction conditions are preferably temperatures in the range of from 20 to 120° C. and pressures of from 20 to 600 psig, more preferably from 45 to 85° C. and 30 to 400 psig, and most preferably from 50 to 80° C. and 40 to 300 psig. The molar ratio of CO:$H_2$ is typically about 1:1, although the ratio can vary considerably. The partial pressure of CO is typically within the range of 5 to 100 psig. The partial pressure of hydrogen is typically within the range of 40 to 200 psig. The reaction is conducted at these conditions until a predominance of the allyl acetate has reacted, e.g. 60 to 99.9%, the products being largely 4-acetoxybutyraldehyde with some branched reaction products. The length of reaction is not critical, but usually a reaction time of 0.5 to 4 hours is adequate.

Preferably, the allyl acetate starting concentration on a reaction solvent to feed basis is in the range of 5 to 40 percent by weight in the solvent; more preferably, a lower concentration in the range of 5 to 10 percent by weight may be used. Preferably, the liquid phase hydrogen:carbon monoxide molar ratio is in the range of from 10:1 to 1:2, more preferably from 5:1 to 1:2.

In the hydroformylation process of the invention, the linear:branched ABA:AMPA product ratio is preferably 20 or greater. The use of a 2,7-dialkyl-9,9-dimethyl-4,5-bis(diphenylphosphino)xanthene has been shown to provide an ABA:AMPA product ratio greater than 60 (see Table 1, Ex. 1C).

Following the hydroformylation step, the hydroformylation products can be separated from the solvent and catalyst by a variety of methods such as water extraction in an extraction vessel. Water extraction methods are well known in the art and can be affected by any suitable means, such as mixer-settlers, packed or trayed extraction columns, rotating disk contactors, or passed to a settling tank for resolution of the mixture into aqueous and organic phases. ABA, and any AMPA, remains soluble in the water (aqueous) phase and is separated from the solvent (organic) phase.

At least a portion of the 4-acetoxybutyraldehyde reaction product may be preferably converted to produce 1,4-butanediol (BDO); any 3-acetoxy-2-methylpropionaldehyde in the reaction product will be converted to 2-methyl-1,3-propanediol (MPD). Preferably, the 4-acetoxybutyraldehyde is hydrolyzed to produce 4-hydroxybutyraldehyde (and co-product acetic acid or an acetate), which is then hydrogenated to produce BDO. The hydrolysis is preferably conducted in water in the presence of a catalyst such as an acid, base, or acidic or basic ion-exchange resin. For instance, the 4-acetoxybutyraldehyde may be hydrolyzed to produce 4-hydroxybutyraldehyde (HBA) in the presence of water and an alkali metal hydroxide. The HBA may then be isolated from the alkali metal acetate by extraction with a suitable solvent such as an alcohol. The alkali metal acetate may be acidified to produce acetic acid.

The 4-hydroxybutyraldehyde may then be hydrogenated in the presence of a hydrogenation catalyst to produce 1,4-butanediol. Hydrogen is added to the reaction vessel for the hydrogenation. Suitable hydrogenation catalysts include any Group VIII metal, such as nickel, cobalt, ruthenium, platinum, and palladium, as well as copper, zinc and chromium and mixtures and alloys thereof. Especially preferred are nickel catalysts. The hydrogenation reaction conditions are preferably temperatures in the range of from 60 to 200° C. and pressures of from 200 to 1000 psig, more preferably from 80 to 140° C. and 300 to 1000 psig. Generally reaction times of 1 to 10 hours are appropriate.

Alternatively, at least a portion of the 4-acetoxybutyraldehyde reaction product may be preferably converted to produce tetrahydrofuran (THF). Preferably, the 4-acetoxybutyraldehyde is hydrogenated to produce 4-acetoxybutanol, which then is dehydroacetoxylated to produce THF. The hydrogenation to produce 4-acetoxybutanol is preferably conducted according to the conditions described above. The 4-acetoxybutanol can then undergo a dehydroacetoxylation reaction to produce THF and acetic acid. The dehydroacetoxylation step is preferably performed at temperatures in the range of from 20 to 300° C. in the presence of a dehydroacetoxylation catalyst, such as silica, silica-alumina, and/or tungsten oxide. A final hydrolysis step may be performed to convert any 3-acetoxy-2-methylpropanol, formed by the hydrogenation of 3-acetoxy-2-methylpropionaldehyde, to 2-methyl-1,3-propanediol (MPD)

BDO (or THF) and MPD are formed while the high ratio of linear to branched products is substantially retained.

The following examples merely illustrate the invention. Those skilled in the art will recognize many variations that are within the spirit of the invention and scope of the claims.

EXAMPLE 1

Preparation of Diphosphines 1A, 1B, and 1C: Diphosphines 1A, 1B, and 1C of the following formulas are prepared as described below.

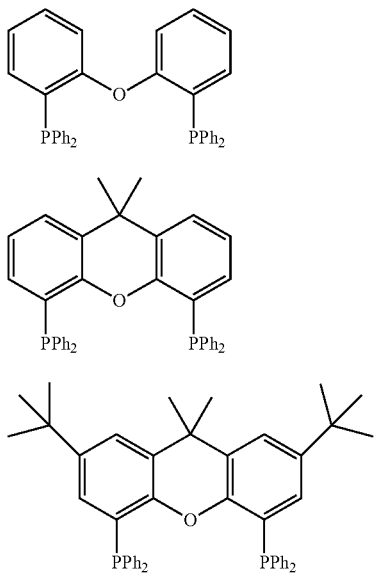

Diphosphine 1A: 2,2'-bis(diphenylphosphino)diphenyl ether.

At room temperature under argon, a solution of sec-BuLi (22 mL, 1.3 mol dm$^{-3}$, 0.029 mol, 3 eq) in hexane is added dropwise to a stirred solution of diphenyl ether (1.6 g, 9.5× 10$^{-3}$ mol, 1 eq) and tetramethylethylenediamine (TMEDA, 3.4 g, 0.029 mol, 3 eq) in dry degassed diethyl ether and stirred for 16 hours. A solution of chlorodiphenylphosphine (5.2 mL, 0.029 mol, 3 eq) in hexane is then added dropwise, and the reaction mixture stirred for a further 16 hours. The solvent is removed under reduced pressure, and the resulting oil dissolved in CH$_2$Cl$_2$, washed with water and dried with MgSO$_4$. The solvent is removed under reduced pressure, and the resulting yellow oil is recrystallized from ethanol to yield 2,2'-bis(diphenylphosphino)diphenyl ether.

Diphosphine 1B: 9,9-dimethyl-4,5-bis(diphenylphosphino)-xanthene, known as XANTPHOS.

Diphosphine 1B is prepared according to the procedure of Diphosphine 1A, except that 9,9-dimethylxanthene (2 g, 9.5× 10$^{-3}$ mol, 1 eq) is used in place of diphenyl ether.

Diphosphine 1C: 2,7-di-tert-butyl-9,9-dimethyl 4,5bis(diphenylphosphino)xanthene.

At −60° C. under argon, a solution of n-BuLi in hexane (5.8 mL, 1.6 mol dm$^{-3}$, 9.2×10$^{-3}$ mol, 2.2 eq) is added dropwise to a solution of 4,5-dibromo-2,7-di-tert-butyl-9,9-dimethylxanthene (2 g, 4.2×10$^{-3}$ mol, 1 eq) in THF (50 mL) and stirred for 1 hour. The reaction mixture is slowly warmed to 0° C., cooled to −60° C. again, and a solution of chlorodiphenylphosphine (1.7 mL, 2.0 g, 9.2×10$^{-3}$ mol, 2.2 eq) in THF (10 mL) was added dropwise under argon. The reaction mixture is warmed to room temperature, the solvent is removed under reduced pressure, and the resulting white residue is dissolved in CH$_2$Cl$_2$, washed with water and dried with MgSO$_4$. The solvent is removed under reduced pressure to give 2,7-di-tert-butyl-9,9-dimethyl-4,5-bis(diphenylphosphino) xanthene (1.3395 g, 2.7×10$^{-3}$, 64% yield) as a white solid.

Comparative Diphosphine 1D: 1,4-bis(diphenylphosphino)butane, known as dppb.

Comparative Diphosphine 1E: 1,1'-bis(diphenylphosphino)-ferrocene, known as dppf.

Comparative Diphosphine 1F: [2,2'-bis(diphenylphosphino)methyl-1,1'-biphenyl], known as BISBI.

Comparative Phosphine 1G: triphenyl phosphine, known as TPP.

EXAMPLE 2

Hydroformylation Reaction using Phosphines

Allyl acetate is hydroformylated using diphosphines 1A-1F and triphenyl phosphine 1G according to the following procedure:

A solution of the desired phosphine (2 equivalents or 8.6× 10$^{-5}$ moles) in dry degassed toluene (15 g) is added to [Rh (CO)$_2$(acac)] (1 equivalent or 4.3×10$^{-5}$ moles) in a 100 mL Parr autoclave. The solution is flushed three times with a 1:1 CO/H$_2$ mixture and then pressurized to 180 psig with the CO/H$_2$ mixture. The autoclave is then heated to 65° C. with stirring, allyl acetate (3.5 mL) is injected, and the autoclave is pressurized to 200 psig with the CO/H$_2$ mixture. The autoclave is kept at a constant pressure of 200 psig, and the gas uptake of the reaction is monitored. When there is no further gas uptake, the autoclave is cooled and depressurized. The resulting solution is analyzed by gas chromatography to determine the products of the reaction. The reaction produces ABA, AMPA, C$_3$ products (acetates of propylene or propane), acetic acid, and butyraldehyde.

The results, shown in Table 1, demonstrate that the 2,2'-bis(dihydrocarbylphosphino)diphenyl ethers of the current invention unexpectedly result in significantly higher ABA:AMPA (l:b) ratio than any other phosphine.

TABLE 1

| | Phosphine Comparisons | | | |
|---|---|---|---|---|
| Diphosphine | Conversion (%) | ABA (%) | AMPA (%) | ABA:AMPA ratio |
| 1A | >99% | 92.2 | 3.9 | 23.6 |
| 1B | >99% | 90.5 | 1.8 | 49.7 |
| 1C | >99% | 88.1 | 1.3 | 67.8 |
| 1D* | >99% | 67.2 | 3.8 | 17.9 |
| 1E* | >99% | 77.6 | 15.5 | 5.0 |
| 1F* | >99% | 65.8 | 13.5 | 4.9 |
| 1G* | >99% | 72.6 | 22.6 | 3.2 |

*Comparative Example

I claim:

1. A process to produce 4-acetoxybutyraldehyde comprising reacting allyl acetate with carbon monoxide and hydrogen in the presence of a solvent and a catalyst comprising a rhodium complex and a substituted or unsubstituted 2,2'-bis(dihydrocarbylphosphino)diphenyl ether.

2. The process of claim 1 wherein the 2,2'-bis(dihydrocarbylphosphino)diphenyl ether is 2,2'-bis(diphenylphosphino) diphenyl ether.

3. The process of claim 1 wherein the 2,2'-bis(dihydrocarbylphosphino)diphenyl ether is a substituted or unsubstituted 4,5-bis(dihydrocarbylphosphino)xanthene.

4. The process of claim 3 wherein the 4,5-bis(dihydrocarbylphosphino)xanthene is 9,9-dimethyl-4,5-bis(diphenylphosphino)xanthene.

5. The process of claim 3 wherein the 4,5-bis(dihydrocarbylphosphino)xanthene is a 2,7-dialkyl-9,9-dimethyl-4,5-bis (diarylphosphino)xanthene.

6. The process of claim 5 wherein the 2,7-dialkyl-9,9-dimethyl-4,5-bis(diarylphosphino)xanthene is 2,7-di-tert-butyl-9,9-dimethyl-4,5-bis(diphenylphosphino)xanthene.

7. The process of claim 1 wherein the solvent is selected from the group consisting of $C_5$-$C_{20}$ aliphatic hydrocarbons, $C_6$-$C_{12}$ aromatic hydrocarbons, ethers, alcohols, and mixtures thereof.

8. The process of claim 1 wherein the solvent is selected from the group consisting of toluene, cyclohexane, methyl t-butyl ether, and mixtures thereof.

9. The process of claim 1 wherein the rhodium complex comprises rhodium and ligands selected from the group consisting of hydride, carbonyl, trialkyl phosphines, triaryl phosphines, cyclopentadienyls, 2,4-alkanedionates, and mixtures thereof.

10. The process of claim 1 wherein the catalyst further comprises a monophosphine compound.

11. The process of claim 1 further comprising converting at least a portion of the 4-acetoxybutyraldehyde to produce 1,4-butanediol.

12. The process of claim 1 further comprising converting at least a portion of the 4-acetoxybutyraldehyde to produce tetrahydrofuran.

* * * * *